(12) United States Patent
Jakobovits (10) Patent No.: US 8,654,139 B2
(45) Date of Patent: Feb. 18, 2014

(54) METHODS AND SYSTEMS TO TRANSMIT, VIEW, AND MANIPULATE MEDICAL IMAGES IN A GENERAL PURPOSE VIEWING AGENT

(75) Inventor: Rex Jakobovits, Seattle, WA (US)

(73) Assignee: McKesson Technologies Inc., Alpharetta, GA (US)

(*) Notice: Subject to any disclaimer, the term of this patent is extended or adjusted under 35 U.S.C. 154(b) by 1020 days.

(21) Appl. No.: 12/201,417

(22) Filed: Aug. 29, 2008

(65) Prior Publication Data

US 2009/0059082 A1 Mar. 5, 2009

Related U.S. Application Data

(60) Provisional application No. 60/968,612, filed on Aug. 29, 2007, provisional application No. 60/984,298, filed on Oct. 31, 2007.

(51) Int. Cl.
*G09G 5/02* (2006.01)

(52) U.S. Cl.
USPC ............................ 345/589; 345/581; 345/617

(58) Field of Classification Search
USPC ............ 345/856; 715/856; 382/132, 240, 232
See application file for complete search history.

(56) References Cited

U.S. PATENT DOCUMENTS

| | | | |
|---|---|---|---|
| 4,945,476 A | 7/1990 | Bodick et al. | |
| 5,542,003 A * | 7/1996 | Wofford | 382/132 |
| 5,583,758 A | 12/1996 | McIlroy et al. | |
| 5,664,109 A | 9/1997 | Johnson et al. | |
| 5,710,835 A | 1/1998 | Bradley | |
| 5,724,070 A | 3/1998 | Denninghoff et al. | |
| 5,835,735 A | 11/1998 | Mason et al. | |
| 5,854,851 A | 12/1998 | Bamberger et al. | |
| 5,953,704 A | 9/1999 | McIlroy et al. | |
| 5,970,164 A | 10/1999 | Bamberger et al. | |
| 6,101,407 A | 8/2000 | Groezinger | |
| 6,167,442 A | 12/2000 | Sutherland et al. | |
| 6,182,029 B1 | 1/2001 | Friedman | |
| 6,260,021 B1 | 7/2001 | Wong et al. | |
| 6,269,193 B1 | 7/2001 | Young et al. | |
| 6,269,379 B1 | 7/2001 | Hiyama et al. | |
| 6,304,277 B1 | 10/2001 | Hoekstra et al. | |
| 6,349,330 B1 | 2/2002 | Bernadett et al. | |
| 6,349,373 B2 | 2/2002 | Sitka et al. | |

(Continued)

FOREIGN PATENT DOCUMENTS

WO WO 2006/118628 A2 11/2006

OTHER PUBLICATIONS

Office Action for U.S. Appl. No. 12/262,714 dated Oct. 6, 2011.
Office Action for U.S. Appl. No. 12/262,714 dated Feb. 14, 2011.

(Continued)

*Primary Examiner* — Phi Hoang
(74) *Attorney, Agent, or Firm* — Alston & Bird LLP (57) ABSTRACT

An apparatus may include a processor configured to determine a first value for a center of brightness and a second value for a window width for contrast. The processor may further be configured to process a first image to generate a second image having a reduced bit-depth based at least in part upon the determined first and second values. The processor may additionally be configured to provide the second image to a remote device to facilitate viewing and manipulation of the second image in a general purpose viewing agent. Corresponding methods, computer program products, and systems are also provided.

18 Claims, 4 Drawing Sheets

(56) References Cited

U.S. PATENT DOCUMENTS

| | | | |
|---|---|---|---|
| 6,424,996 | B1 | 7/2002 | Killcommons et al. |
| 6,493,702 | B1 | 12/2002 | Adar et al. |
| 6,564,256 | B1 | 5/2003 | Tanaka |
| 6,574,629 | B1 | 6/2003 | Cooke, Jr. et al. |
| 6,633,674 | B1 | 10/2003 | Barnes et al. |
| 6,678,703 | B2 | 1/2004 | Rothschild et al. |
| 6,792,151 | B1 | 9/2004 | Barnes et al. |
| 6,795,583 | B1 | 9/2004 | Barnes et al. |
| 6,912,317 | B1 | 6/2005 | Barnes et al. |
| 6,934,698 | B2 | 8/2005 | Judd et al. |
| 6,968,077 | B1 | 11/2005 | Yamanaka |
| 6,987,945 | B2 | 1/2006 | Corn et al. |
| 6,988,240 | B2 | 1/2006 | Gröber et al. |
| 7,039,723 | B2 | 5/2006 | Hu et al. |
| 7,047,235 | B2 | 5/2006 | Yang et al. |
| 7,080,098 | B2 | 7/2006 | Smirniotopoulos et al. |
| 7,106,479 | B2 | 9/2006 | Roy et al. |
| 7,106,890 | B1 | 9/2006 | Grant et al. |
| 7,127,445 | B2 | 10/2006 | Mogi et al. |
| 7,171,625 | B1 | 1/2007 | Sacchi |
| 7,181,617 | B2 | 2/2007 | Wise et al. |
| 7,194,474 | B2 | 3/2007 | Birdwell et al. |
| 7,280,702 | B2 * | 10/2007 | Chang et al. ............. 382/240 |
| 7,440,626 | B2 | 10/2008 | Kong et al. |
| 7,457,656 | B2 | 11/2008 | Judd et al. |
| 8,055,636 | B2 | 11/2011 | Judd et al. |
| 8,520,978 | B2 | 8/2013 | Jakobovits |
| 2001/0019587 | A1 | 9/2001 | Hashimoto et al. |
| 2001/0048734 | A1 * | 12/2001 | Uppaluri et al. ............. 378/207 |
| 2002/0059288 | A1 | 5/2002 | Yagi et al. |
| 2002/0167552 | A1 * | 11/2002 | Senda ............. 715/856 |
| 2003/0061071 | A1 | 3/2003 | Babula et al. |
| 2004/0005094 | A1 | 1/2004 | Huffman |
| 2004/0107118 | A1 | 6/2004 | Harnsberger et al. |
| 2004/0141661 | A1 | 7/2004 | Hanna et al. |
| 2004/0143645 | A1 | 7/2004 | Cheenath |
| 2004/0170308 | A1 * | 9/2004 | Belykh et al. ............. 382/128 |
| 2004/0249806 | A1 | 12/2004 | Kanada |
| 2005/0005241 | A1 | 1/2005 | Hunleth et al. |
| 2005/0021780 | A1 | 1/2005 | Beyda |
| 2005/0043966 | A1 | 2/2005 | Harnsberger et al. |
| 2005/0108052 | A1 | 5/2005 | Omaboe |
| 2005/0108058 | A1 | 5/2005 | Weidner et al. |
| 2005/0108365 | A1 | 5/2005 | Becker et al. |
| 2005/0129319 | A1 | 6/2005 | Lee et al. |
| 2005/0237324 | A1 | 10/2005 | Guhring |
| 2005/0251012 | A1 | 11/2005 | Judd et al. |
| 2005/0271283 | A1 * | 12/2005 | Dekel et al. ............. 382/232 |
| 2006/0020622 | A1 | 1/2006 | Shelton |
| 2006/0025670 | A1 | 2/2006 | Kim et al. |
| 2006/0025671 | A1 | 2/2006 | Kusunoki |
| 2006/0082809 | A1 | 4/2006 | Loukipoudis et al. |
| 2006/0112142 | A1 | 5/2006 | Sako et al. |
| 2006/0168338 | A1 | 7/2006 | Bruegl et al. |
| 2006/0170693 | A1 | 8/2006 | Bethune et al. |
| 2006/0210196 | A1 | 9/2006 | Wensley et al. |
| 2006/0229911 | A1 | 10/2006 | Gropper et al. |
| 2006/0242148 | A1 | 10/2006 | Rothpearl et al. |
| 2006/0274928 | A1 | 12/2006 | Collins et al. |
| 2007/0035551 | A1 | 2/2007 | Ubillos |
| 2007/0052716 | A1 * | 3/2007 | Jabri et al. ............. 345/581 |
| 2007/0067184 | A1 | 3/2007 | Harp et al. |
| 2007/0067252 | A1 * | 3/2007 | Hengerer et al. ............. 707/1 |
| 2007/0118540 | A1 | 5/2007 | Guo |
| 2007/0118550 | A1 | 5/2007 | Yang et al. |
| 2007/0208994 | A1 | 9/2007 | Reddel et al. |
| 2008/0025583 | A1 | 1/2008 | Jabri et al. |
| 2008/0084415 | A1 | 4/2008 | Gundel |
| 2008/0120142 | A1 | 5/2008 | Jakobovits |
| 2008/0140722 | A1 | 6/2008 | Jakobovits |
| 2008/0285711 | A1 * | 11/2008 | Avinash et al. ............. 378/22 |
| 2009/0028398 | A1 * | 1/2009 | Lundstrom ............. 382/128 |
| 2009/0132285 | A1 | 5/2009 | Jakobovits |
| 2009/0274384 | A1 | 11/2009 | Jakobovits |
| 2010/0063992 | A1 | 3/2010 | Ma et al. |
| 2011/0110568 | A1 | 5/2011 | Vesper et al. |
| 2012/0191793 | A1 | 7/2012 | Jakobovits |

OTHER PUBLICATIONS

Garrett, J. J., *Ajax: A New Approach to Web Applications*, Published by Adaptive Path, Feb. 18, 2005, 5 pages.
Supplementary European Search Report for Appl. No. EP 07 86 4684 mailed Mar. 11, 2010.
Office Action for U.S. Appl. No. 11/943,355 dated Apr. 26, 2011.
Office Action in U.S. Appl. No. 11/943,388 dated Aug. 19, 2010.
Office Action mailed Sep. 30, 2010, for U.S. Appl. No. 11/943,355.
Jayalath, R. et al., "Quantification of Abdominal Aortic Calcification on CT", American Heart Association, Feb. 2006, pp. 429-430.
Sachs, J., "Image Resampling", Digital Light & Color, 2001.
Transmittal of International Preliminary Report on Patentability for International Application No. PCT/US2007/085292 mailed Jun. 4, 2009.
Notification of Transmittal of the International Search Report and the Written Opinion for International Application No. PCT/US07/85292 mailed May 20, 2008.
Non-Final Office Action for U.S. Appl. No. 11/943,388 dated Jan. 29, 2010.
Office Action for U.S. Appl. No. 11/943,355, mailed Feb. 27, 2012.
Office Action for U.S. Appl. No. 12/262,668 mailed Dec. 15, 2011.
Digital Imaging & Communications in Medicine (DICOM), Part 9, Communication Support for Message Exchange (National Electrical Manufacturers Association, Copyright 2007); 68 pages.
Office Action for U.S. Appl. No. 11/943,388, mailed May 16, 2012.
Balani, N., et. al, "Build apps using Asynchronous JavaScript with XML (AJAX)", Nov. 15, 2005, IBM.
Green, B.C.; , "Web Access to DICOM Objects ("WADO")", May 1, 2009, UtraRAD Corporation.
Murray, G.; "Asynchronous JavaScript Technology and XML (AJAX) With the Java Platform", Oct. 2006, Oracle.
Powell, M.; "Asynchronous Web Service Calls over HTTP with the .NET Framework", Sep. 9, 2002, Microsoft.
Kaldoudi, et al.; "*A Service Based Approach for Medical Image Distribution in Healthcare Internets;*" Computer Methods and Programs in Biomedicine, vol. 81, No. 2; pp. 117-127; dated Sep. 2, 2005.
Koutelakis, et al.; "*PACS through Web Compatible with DICOM Standard and WADO Service Advantiages and Implementation;*" EMBS Annual International Conference; dated Sep. 3, 2008.
Office Action for U.S. Appl. No. 11/943,388; dated Feb. 8, 2013.
Office Action for U.S. Appl. No. 12/201,417; dated May 24, 2012.
Office Action from U.S. Appl. No. 12/262,714, mailed Jul. 30, 2012.
Koichi et al., *Longitidinal Storage of Medical Images Using Transformation of DICOM to JPEG*, Dialog/2004 Japan Science and Tech Corp (JST), abstract, partial, p. 1, available at http://sciencelinks.jp/j-east/article/200120/000020012001A0334475.php.
DICOM Standards Committee, Working Group 6, Digital Imaging and Communications in Medicine (DICOM) Supplement 113—Email Transport, Aug. 24, 2006.
Office Action for U.S. Appl. No. 12/262,714 dated May 24, 2013.
Office Action for U.S. Appl. No. 12/262,668 dated Jul. 20, 2012.
Office Action for U.S. Appl. No. 12/262,668 dated Mar. 29, 2013.
Notice of Allowance for U.S. Appl. No. 12/262,668 dated May 7, 2013.
Office Action for U.S. Appl. No. 13/434,959 dated Oct. 29, 2012.
Office Action for U.S. Appl. No. 13/434,959 dated Mar. 14, 2013.
Office Action for U.S. Appl. No. 13/434,959 dated Sep. 23, 2013.

* cited by examiner

METHODS AND SYSTEMS TO TRANSMIT, VIEW, AND MANIPULATE MEDICAL IMAGES IN A GENERAL PURPOSE VIEWING AGENT

CROSS-REFERENCE TO RELATED APPLICATIONS

This application claims priority from U.S. Provisional Application No. 60/968,612, filed Aug. 29, 2007, entitled METHODS AND SYSTEMS TO TRANSMIT, VIEW, AND MANIPULATE MEDICAL IMAGES IN A WEB BROWSER USING FLASH AND RELATED TECHNOLOGIES, the contents of which are incorporated herein by reference and from U.S. Provisional Application No. 60/984,298, filed Oct. 31, 2007, entitled METHODS AND SYSTEMS TO MANAGE, VIEW, MANIPULATE, SHARE AND ANNOTATE IMAGES IN A WEB BROSWER.

TECHNOLOGICAL FIELD

Embodiments of the present invention relate generally to tools, methods, and systems for managing, viewing, manipulating, sharing, and annotating images in a general purpose viewing agent, such as a web browser.

BACKGROUND

Advances in processor, networking and other related technologies have led to increased networked computing, and abundant availability of content on private and public networks. Users may access the available content from computing devices remote from the content storage and interact with the content using their local computing device. A particularly relevant example is medical imaging, in which radiologists and other physicians may access and manipulate medical images as part of diagnostic interpretation. However, today, managing, viewing, manipulating, sharing and annotating images often requires specialized software. Even where such managing, viewing, manipulating, sharing and annotating of images may currently be performed over a general purpose viewing agent, such as a web browser, the general purpose viewing agent often requires usage and/or installation of special add-on or plug-in software components to the web browser, such as Applets or ActiveX technology. In this regard, existing web-based imaging systems may be limited in their imaging functionality, and/or may not be "true thin client" as they require software to be installed and maintained on every computer, which incurs high support and maintenance costs. With an ActiveX-based system, accessing an image may involve installation of software that requires administrative privileges and changing default browser security settings. Java Applet-based systems may suffer performance limitations and require pre-installation of the Java runtime environment, which may be a difficult and laborious process.

In many environments where medical images are viewed, it is often not convenient to load Applets or ActiveX components that are not already installed in the browser due to security constraints, performance issues, and/or managed deployment constraints. In particular, the "friction" of installing and maintaining these applications makes them less than ideal in a medical context for remote consultation or communicating findings with referring physicians at third party institutions. Some prior attempts have been made to offer a thin client through the use of animated Graphic Interchange Format (GIF) images, however animated GIFs cannot be manipulated manually and accordingly are not suitable for general purpose diagnostics, which require features such as dynamic zoom/pan and adjusting window/level settings. Accordingly, it may be advantageous to provide methods, apparatuses, computer program products, and systems that allow for remote viewing, managing, manipulating, sharing, and annotating data, such as images, using a general purpose viewing agent, such as a web browser, without requiring the download and installation of specialized software.

BRIEF SUMMARY OF SOME EXAMPLES OF THE INVENTION

Methods, apparatuses, computer program products, and systems are therefore provided, which may provide for managing, viewing, manipulating, sharing, and annotating images in a general purpose viewing agent, such as a web browser. In this regard, embodiments of the invention may provide a rich user interface without requiring software to be downloaded and installed on a general purpose viewing agent, such as a web browser, beyond what is already present on a large majority of browsers. Accordingly, embodiments of the present invention may work instantly with any browser on any platform, without requiring installation of additional specialized software components.

In this regard, embodiments of the present invention may provide a general solution that leverages general purpose viewing agents along with general graphics/animation services that are either natively available or which are widely installed in general purpose viewing agents. Such general graphics/animation services may include, for example, Adobe® Flash®, Adobe® Flex®, and Microsoft® Silverlight™, as well as markup and scripting languages, such as pure HTML, Javascript, and/or related technologies for managing, viewing, and manipulating images over the web and communicating with a data server. Embodiments may also use "Asynchronous Flash, Javascript, and/or related technologies and XML" (Ajax) to manipulate the browser and communicate with the server asynchronously. Embodiments of the invention are unique in that they do not require the client to download or install any software (if an appropriate general graphics/animation service, such as, for example, Flash®, is already installed), and so it is much easier to deploy, access, and maintain than other methods.

Embodiments of the invention may enable users to retrieve images from a server, view annotations, adjust image properties such as brightness and contrast (or window width and level), navigate up and down through a stack of images, zoom in and pan around on images, draw annotation layers on the images, and save annotations back to the server. Images may be dynamically resized to fit the resolution of the viewing window, and higher resolution images are automatically retrieved from the server when the image is enlarged. These features may rely on user interface functionality that is not usually found in pure web applications, e.g. drag and drop, dynamic image manipulation, and instantaneous updates to the current web page without requiring a browser refresh.

In one exemplary embodiment, a method is provided which may include determining a first value for a center of brightness and a second value for a window width for contrast. The method may further include processing a first image to generate a second image having a reduced bit-depth based at least in part upon the determined first and second values. The method may also include providing the second image to a remote device to facilitate viewing and manipulation of the second image in a general purpose viewing agent.

In another exemplary embodiment, a computer program product is provided. The computer program product includes at least one computer-readable storage medium having computer-readable program instructions stored therein. The computer-readable program instructions may include first, second, and third program instructions. The first program instruction is for determining a first value for a center of brightness and a second value for a window width for contrast. The second program instruction is for processing a first image to generate a second image having a reduced bit-depth based at least in part upon the determined first and second values. The third program instruction is for providing the second image to a remote device to facilitate viewing and manipulation of the second image in a general purpose viewing agent.

In another exemplary embodiment, an apparatus is provided, which may include a processor. The processor may be configured to determine a first value for a center of brightness and a second value for a window width for contrast. The processor may further be configured to process a first image to generate a second image having a reduced bit-depth based at least in part upon the determined first and second values. The processor may additionally be configured to provide the second image to a remote device to facilitate viewing and manipulation of the second image in a general purpose viewing agent.

In another exemplary embodiment, a system is provided that may comprise a host device and a client device. The host device may be configured to receive a request for a medical image from a client device, determine a first value for a center of brightness and a second value for a window width for contrast, process the requested medical image to generate a second image having a reduced bit-depth based at least in part upon the determined first and second values, and provide the second image to the client device. The client device may be configured to request a medical image from the host device and to receive the second image, wherein the client device comprises a general purpose general purpose viewing agent for facilitating viewing and manipulation of the second image by a user of the client device.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

Figure 1:
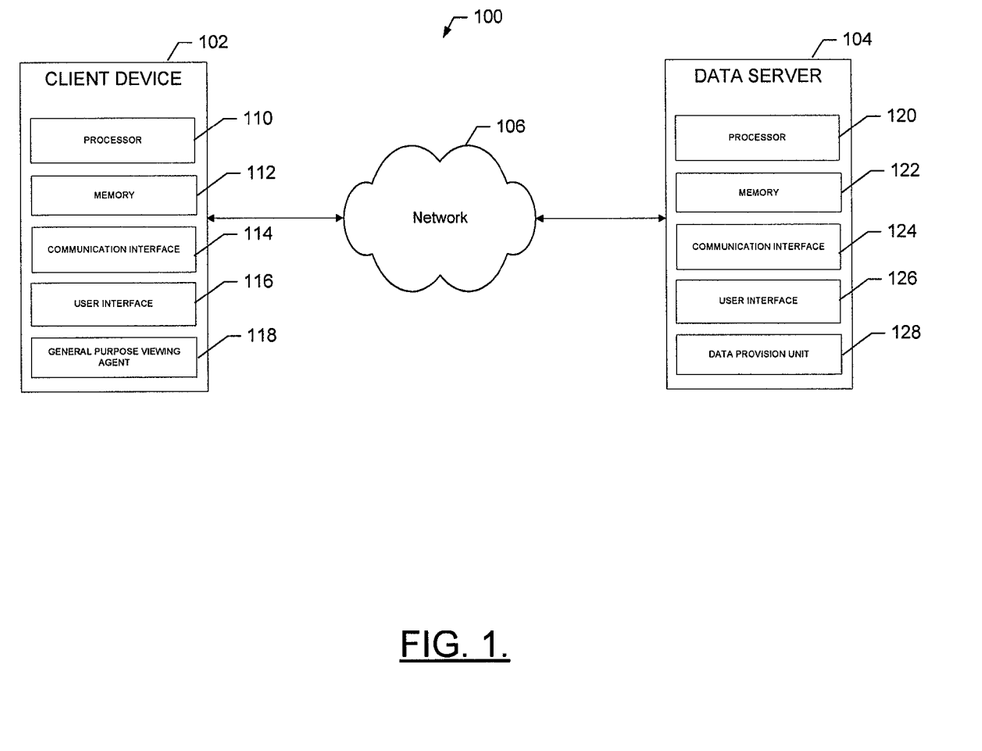
FIG. 1 illustrates a block diagram of a system for transmitting, viewing, and manipulating medical images according to an exemplary embodiment of the present invention.
Figure 2:
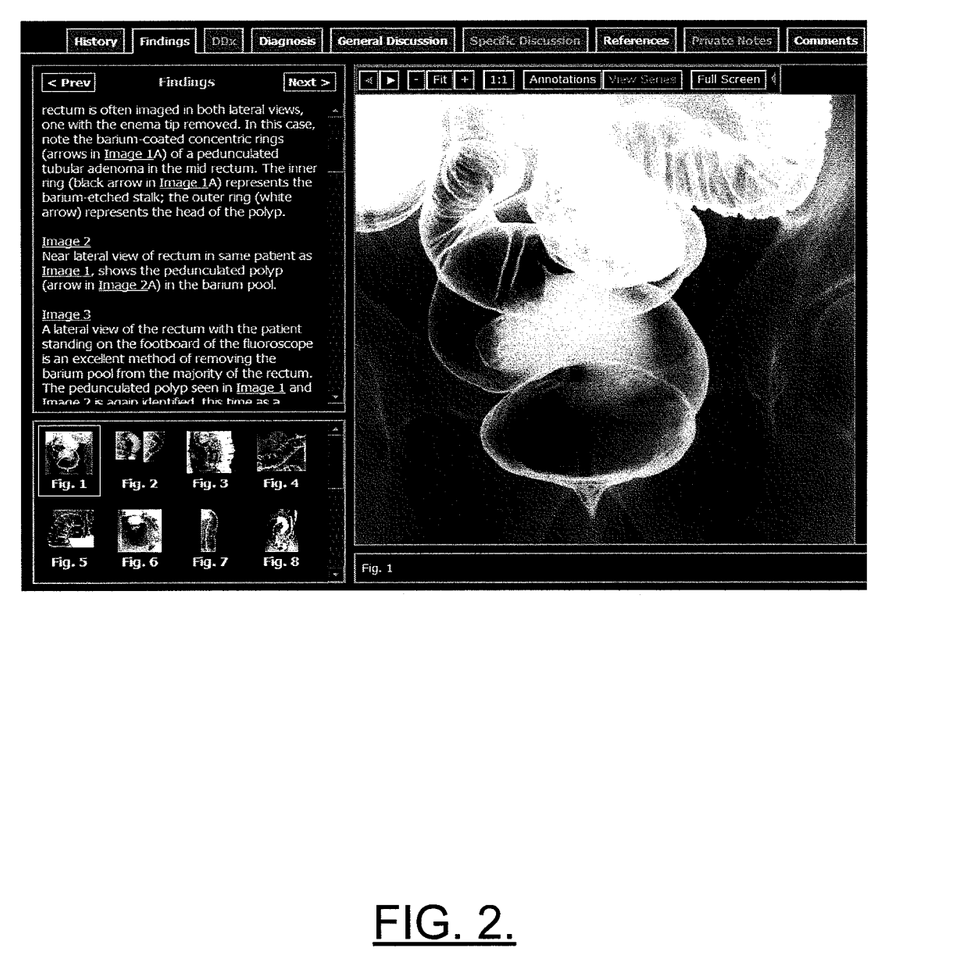
FIG. 2 illustrates a screenshot of a medical image and associated data, such as may be viewed and manipulated using embodiments of the present invention.

FIG. 1 illustrates a block diagram of a system 100 for viewing and manipulating data, such as, for example, images, according to an exemplary embodiment of the present invention. An example of an image that may be viewed and manipulated by the system 100 is illustrated in FIG. 2, which illustrates a case viewer, such as may be viewed within a general purpose viewing agent, with an image viewer and viewed image on the right. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein. As such, while FIG. 1 illustrates one example of a configuration of a system for viewing and manipulating images, numerous other configurations may also be used to implement embodiments of the present invention.

As used herein, "general purpose viewing agent" refers to any means, such as may be embodied in software, hardware, firmware, or some combination thereof that may be used to access, view, and interact with content. Such content may be located remotely from the computing device on which the general purpose viewing agent is embodied and may be accessed by the general purpose viewing agent over a network, such as the internet. In an exemplary embodiment, a general purpose viewing agent may be a web browser. Further, a general purpose viewing agent as used herein may implement one or more general graphics/animation services, which are generically described to be included as part of a "general purpose viewing agent" as used herein. A "general graphics/animation service" refers to any markup or scripting language that may be implemented by a general purpose viewing agent as well as any plug-in that may be installed in a general purpose viewing agent that is generally configured for a wide range of content viewing purposes and not specifically configured for a limited purpose or application. Such general graphics/animation services may include, for example, Adobe® Flash®, Adobe® Flex®, and Microsoft® Silverlight™, as well as markup and scripting languages, such as pure HTML, Javascript, Ajax, and/or related technologies for managing, viewing, and manipulating images over the web and communicating with a data server. Thus, general graphics/animation services do not include special purpose ActiveX components or Java applets.

Referring again to FIG. 1, the system 100 may include a client device 102 and data server 104 configured to communicate over a network 106. The client device 102 may be embodied as any computing device, mobile or fixed, and may be embodied as a server, desktop computer, laptop computer, mobile terminal, and/or the like configured to communicate with the data server 104 over the network 106. The data server 104 may be embodied as any computing device or plurality of computing devices configured to provide data to a client device 102 over a network 106 as will be described further herein below. In this regard, the data server 104 may be embodied, for example, as a server cluster and/or may be embodied as a distributed computing system, such as may be distributed across a plurality of computing devices. Although referred to herein as a "server," it will be appreciated that the data server 104 may be embodied as a computing device other than a server. In an exemplary embodiment, the data server 104 may comprise a Picture Archiving and Communication System (PACS). Further, although only a single client device 102 and data server 104 are illustrated in FIG. 1, the system 100 may comprise a plurality of client devices 102 and data servers 104.

Figure 3:
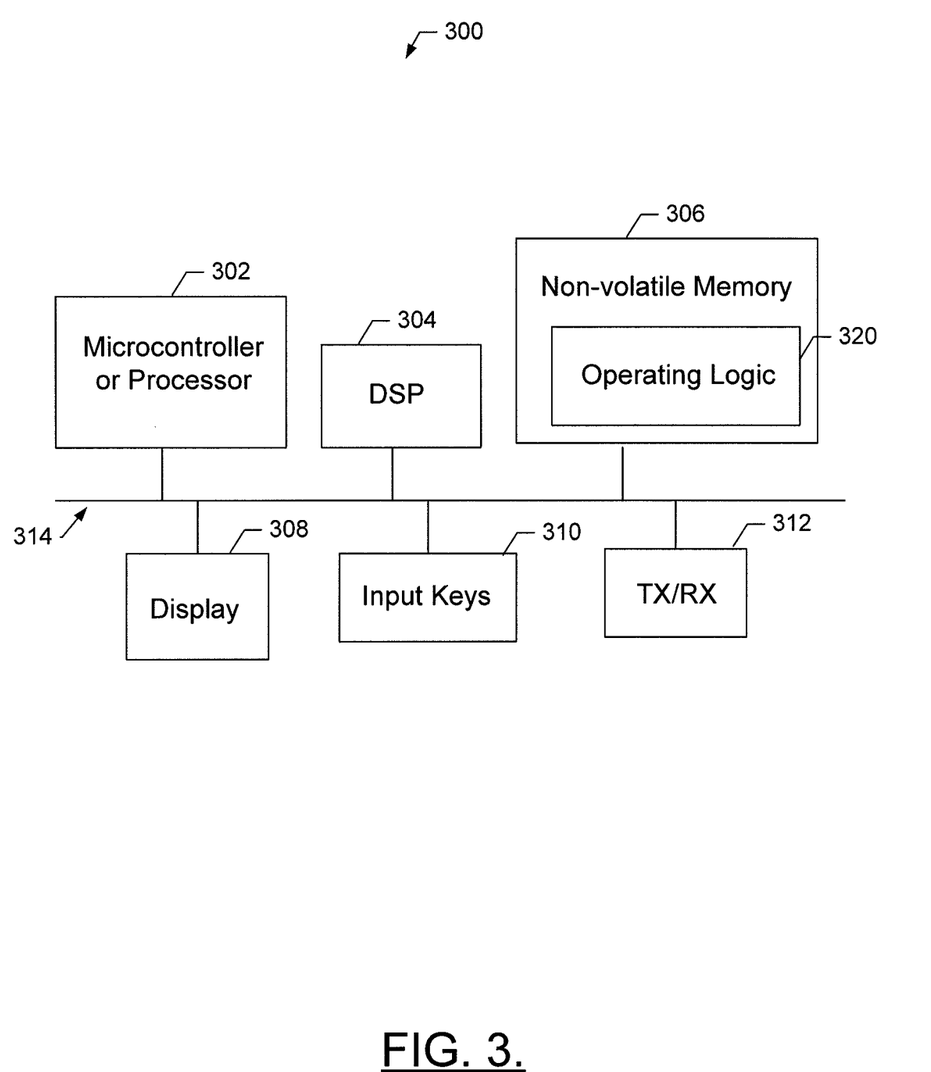
FIG. 3 illustrates a block diagram of a computing architecture suitable for practicing aspects of embodiments of the present invention.

The client device 102 and data server 104 may comprise an architecture 300 illustrated in FIG. 3. The computing architecture 300 suitable for practicing aspects of embodiments of the present invention. The architecture 300 may include various means, such as micro-controller/processor 302, digital signal processor (DSP) 304, non-volatile memory 306, display 308, input keys 310 (e.g., 12 key pad, select button, D-unit), and/or transmit/receive unit (TX/RX) 312, coupled to each other via bus 314, which may be a single bus or an hierarchy of bridged buses. Further, non-volatile memory 306 may include operating logic 320 adapted to implement operations for practicing various embodiments of the present invention for managing, viewing, manipulating, sharing, and annotating images in a general purpose viewing agent, such as a web browser. The implementation of the operating logic 320 may be via any one of a number programming languages, assembly, C, and so forth.

Returning to FIG. 1, the network 106 may be any network over which the programmer device 102 and data server 104 are configured to communicate. Accordingly, the network 106 may comprise one or more public and/or private wireless networks, wireline networks, or any combination thereof, and in some embodiments may comprise the internet. The network 106 may further comprise a structured network, ad hoc network, or some combination thereof. The network 106 may further utilize any communications protocol or combination of communications protocols that may facilitate inter-device communication between the client device 102 and data server 104.

The client device 102 may include various means, such as a processor 110, memory 112, communication interface 114, user interface 116, and general purpose viewing agent 118 for performing the various functions herein described. These means of the client device 102 may communicate over a bus, such as the bus 314, and may be embodied as, for example, hardware elements (e.g., a suitably programmed processor, combinational logic circuit, and/or the like), computer code (e.g., software or firmware) embodied on a computer-readable medium (e.g. memory 112) that is executable by a suitably configured processing device, or some combination thereof. The processor 110 may, for example, be embodied as various means including a microprocessor, a coprocessor, a controller, or various other processing elements including integrated circuits such as, for example, an ASIC (application specific integrated circuit) or FPGA (field programmable gate array). Accordingly, the processor 110 may comprise the microcontroller 302 and/or the DSP 304 of the architecture 300. In an exemplary embodiment, the processor 110 may be configured to execute instructions stored in the memory 112 or otherwise accessible to the processor 110. Although illustrated in FIG. 1 as a single processor, the processor 110 may comprise a plurality of processors operating in parallel, such as a multi-processor system.

The memory 112 may include, for example, volatile and/or non-volatile memory, such as the non-volatile memory 306. The memory 112 may be configured to buffer input data for processing by the processor 110. Additionally or alternatively, the memory 112 may be configured to store instructions for execution by the processor 110. The memory 112 may comprise one or more databases that store information in the form of static and/or dynamic information. The memory 112 may store, for example, operating logic for applications, such as, for example, a general purpose viewing agent as well as locally cached data, such as images, received from the data server 104. This stored information may be stored and/or used by the general purpose viewing agent 118 during the course of performing its functionalities.

The communication interface 114 may be embodied as any device or means embodied in hardware, software, firmware, or a combination thereof that is configured to receive and/or transmit data from/to a network and/or any other device or module in communication with the client device 102. In one embodiment, the communication interface 114 may be at least partially embodied as or otherwise controlled by the processor 110. In this regard, the communication interface 114 may include, for example, an antenna, a transmitter, a receiver, a transceiver and/or supporting hardware or software for enabling communications with other entities of the system 100, such as a data server 104 via the network 106. Accordingly, the communication interface 114 may be embodied as or comprise elements of the TX/RX 312. The communication interface 114 may be configured to receive and/or transmit data using any protocol that may be used for communications between the client device 102 and data server 104 over the network 106. The communication interface 114 may additionally be in communication with the memory 112, user interface 116, and/or general purpose viewing agent 118.

The user interface 116 may be in communication with the processor 110 to receive an indication of a user input and/or to provide an audible, visual, mechanical, or other output to the user. As such, the user interface 116 may include, for example, a keyboard (e.g., input keys 310), a mouse, a joystick, a display (e.g., display 308), a touch screen display, a microphone, a speaker, and/or other input/output mechanisms. Accordingly, the user interface 116 may be configured to display data, such as images, received from a data server 104 and facilitate user interaction and manipulation with displayed data by receiving from a user of the client device 102 commands and/or queries related to viewing and manipulation of data. The user interface 116 may further be in communication with the memory 112, communication interface 114, and/or general purpose viewing agent 118.

The general purpose viewing agent 118 may be embodied as various means, such as hardware, software, firmware, or some combination thereof and, in one embodiment, may be embodied as or otherwise controlled by the processor 110. In embodiments where the general purpose viewing agent 118 is embodied separately from the processor 110, the general purpose viewing agent 118 may be in communication with the processor 110. In an exemplary embodiment, the general purpose viewing agent 118 may comprise a general purpose viewing agent configured to implement one or more general graphics/animation services and may comprise elements of operating logic 320.

The general purpose viewing agent 118 may be configured to provide means for requesting data, such as an image, from the data server 104. The data may be stored on memory 122 of the data server 104 or on memory of another remote computing device accessible by the data server 104. The requested data may be stored remotely in a format in accordance with the Digital Imaging and Communications in Medicine (DI-COM) standard data format. The general purpose viewing agent 118, however, may not be configured to natively display a full resolution DICOM image. Accordingly, the general purpose viewing agent 118 may be configured to receive requested data from the data server 104 that has been processed to be viewable on the general purpose viewing agent 118. The received processed data may comprise a medical DICOM image with a reduced bit-depth relative to the bit-depth of the original remotely stored images (e.g., 12-bit or 16-bit). In this regard, the received processed image may comprise a reduced-grayscale snapshot of the requested higher-bit image. The gray shades may be mapped from the higher bit to the lower bit pallet based at least in part upon a center of brightness value and a window width value for contrast. The received processed image may be converted into another data format that is viewable using the general purpose viewing agent, such as, for example, the Joint Photographic Experts Group (JPEG) format. In an exemplary embodiment, the general purpose viewing agent 118 may be configured to send values for the center of brightness value and window width value for contrast to the data server 104 in conjunction with the original data request. In this regard, the general purpose viewing agent 118 may be configured to receive a manual selection from a user of the client device 102 over the user interface 116 indicating a first desired value for a center of brightness and/or a second desired value for a window width for contrast. Additionally or alternatively, the general purpose viewing agent 118 may be configured to store a default setting, such as in memory 112 for a first value for a center of brightness and/or a second value for a window width for contrast and may send the stored default values to the data server 104 with the data request.

The general purpose viewing agent 118 may further be configured to facilitate manipulation a received image by a user of the client device 102. Such manipulation may be facilitated by a general graphics/animation service, such as Flash® included in or otherwise supported by the general purpose viewing agent 118 as previously described. For example, a user may adjust the brightness and contrast by providing input to the general purpose viewing agent 118 over the user interface 116. The input may comprise a user selecting to adjust the brightness and/or contrast using a graphical user interface (GUI) displayed by the data viewing agent 118. Additionally or alternatively, the input may comprise a user dragging a cursor across a display screen, such as with a mouse, horizontally, vertically, or some combination thereof to adjust the brightness and/or contrast of the displayed image.

Adjustments of brightness and contrast levels of an image displayed by the general purpose viewing agent 118 are of course limited to the range of the current reduced bit snapshot of the original image. However, the range of the current snapshot may not be suitable for the User's needs. In an exemplary embodiment of the invention, if the user wants to go beyond the ranges in the reduced bit snapshot, the user may cause a new reduced bit snapshot to be processed by the data server 104 from the original higher-bit image. In this regard, a user may manually select from a GUI displayed by the general purpose viewing agent 118 to have a new reduced-bit snapshot of the original created and may provide new values for a center of brightness and/or a window width for contrast. The general purpose viewing agent 118 may be configured to then send the new request to the data server 104 and receive the newly processed reduced-bit snapshot from the data server 104. Additionally or alternatively, the general purpose viewing agent 118 may be configured to automatically request a new reduced-bit snapshot from the data server 104 when a user attempts to adjust brightness and/or contrast levels beyond the ranges allowable by the presently displayed image and/or beyond a predefined threshold within the ranges provided by the presently displayed image. In such an embodiment, the general purpose viewing agent 118 may be configured to send the request with a new value for a center of brightness and/or a new value for a window width for contrast based at least in part upon a predefined offset from a value in range of brightness and/or contrast of the currently displayed reduced-bit image. The general purpose viewing agent 118 may then receive the newly processed reduced-bit image and replace the existing image with the newly received image so as to allow the user to then manipulate the new image as described previously. Accordingly, the general purpose viewing agent may be configured to seamlessly replace the existing image with the new image so as to provide the user an approximation to a full range of adjustment that would be permissible if the general purpose viewing agent 118 were able to support the image of higher bit depth of the original remotely stored image natively.

In an exemplary embodiment, the general purpose viewing agent 118 may be configured to receive and process a data stream, such as hypertext transfer protocol (HTTP) stream, received from the data server 104. The received data stream may contain delimited messages and the general purpose viewing agent 118 may be configured to handle the delimited messages independently. Accordingly, the general purpose viewing agent 118 may not need to wait for the requested data to be received and parsed in its entirety before taking action on the individual delimited messages. For example, if the general purpose viewing agent 118 is waiting to receive one or more images, such as a series of images, as they are being processed and created on the data server 104, rather than waiting for all of the images in a series to be created, the general purpose viewing agent 118 may receive messages from the data server 104 that are delimited by a defined character sequence and the general purpose viewing agent 118 may process those messages independently and retrieve the images as they are created. Additionally, if the general purpose viewing agent 118 may receive a single requested image as a series of delimited messages and may render the received image as the messages are received from the data server rather than waiting for the entire image to be received. These delimited messages may, for example, help facilitate seamless replacement of a first reduced bit-depth image with a second reduced bit-depth image as portions of the image may be replaced as the delimited messages arrive.

Referring now to the data server 104, the data server 104 may include various means, such as a processor 120, memory 122, communication interface 124, user interface 126, and/or data provision unit 120 for performing the various functions herein described. These means of the data server 104 may communicate over a bus, such as the bus 314, and may be embodied as, for example, hardware elements (e.g., a suitably programmed processor, combinational logic circuit, and/or the like), computer code (e.g., software or firmware) embodied on a computer-readable medium (e.g. memory 122) that is executable by a suitably configured processing device, or some combination thereof. The processor 120 may, for example, be embodied as various means including a microprocessor, a coprocessor, a controller, or various other processing elements including integrated circuits such as, for example, an ASIC (application specific integrated circuit) or FPGA (field programmable gate array). Accordingly, the processor 120 may comprise the microcontroller 302 and/or the DSP 304 of the architecture 300. In an exemplary embodiment, the processor 120 may be configured to execute instructions stored in the memory 122 or otherwise accessible to the processor 110. Although illustrated in FIG. 1 as a single processor, the processor 120 may comprise a plurality of processors operating in parallel, such as a multi-processor system. These multiple processors may be embodied on a single computing device or may be distributed across multiple computing devices, such as, for example, a server cluster, rack of blade servers, or a distributed computing system.

The memory 122 may include, for example, volatile and/or non-volatile memory, such as the non-volatile memory 306. The memory 122 may be configured to buffer input data for processing by the processor 120. Additionally or alternatively, the memory 122 may be configured to store instructions for execution by the processor 120. The memory 122 may comprise one or more databases that store information in the form of static and/or dynamic information. The memory 122 may store, for example, operating logic for applications, as well as data, such as images (e.g. DICOM files), that may be requested by and/or provided to a client device 102. This stored information may be stored and/or used by the data provision unit 128 during the course of performing its functionalities.

The communication interface 124 may be embodied as any device or means embodied in hardware, software, firmware, or a combination thereof that is configured to receive and/or transmit data from/to a network and/or any other device or module in communication with the data server 104. In one embodiment, the communication interface 124 may be at least partially embodied as or otherwise controlled by the processor 120. In this regard, the communication interface 124 may include, for example, an antenna, a transmitter, a receiver, a transceiver and/or supporting hardware or software for enabling communications with other entities of the system 100, such as a client device 102 via the network 106. Accordingly, the communication interface 124 may be embodied as or comprise elements of the TX/RX 312. The communication interface 124 may be configured to receive and/or transmit data using any protocol that may be used for communications between the client device 102 and data server 104 over the network 106. The communication interface 124 may additionally be in communication with the memory 122, user interface 126, and/or data provision unit 128.

The user interface 126 may be in communication with the processor 120 to receive an indication of a user input and/or to provide an audible, visual, mechanical, or other output to the user. As such, the user interface 126 may include, for example, a keyboard (e.g., input keys 310), a mouse, a joystick, a display (e.g., display 308), a touch screen display, a microphone, a speaker, and/or other input/output mechanisms. The user interface 116 may further be in communication with the memory 112, communication interface 114, and/or general purpose viewing agent 118. However, in embodiments wherein the data server 104 functions solely to receive data requests from a client device 102 and provide data to a client device 102, the user interface 126 may be limited or even eliminated.

The data provision unit 128 may be embodied as various means, such as hardware, software, firmware, or some combination thereof and, in one embodiment, may be embodied as or otherwise controlled by the processor 120. In embodiments where the data provision unit 128 is embodied separately from the processor 120, the data provision unit may be in communication with the processor 120. The data provision unit 128 may be configured to receive a request for data, such as an image from a client device 102. The data provision unit 128 may further be configured to retrieve the requested data from a memory (e.g., memory 122 and/or a remote memory that is accessible by the data server 104) in response to the received request.

If the requested data is an image stored in a DICOM or other high resolution format that is not viewable by a general purpose viewing agent, the data provision unit 128 may be configured to process the retrieved requested image to generate a second image having a reduced bit-depth such that the second image is viewable in a general purpose viewing agent 118. The second image may be formatted in accordance with a protocol standard to a general purpose viewing agent 118, such as, for example a JPEG image. Thus the processed image may comprise a reduced-grayscale snapshot of the requested higher-bit image. The gray shades may be mapped from the higher bit to the lower bit pallet based at least in part upon a center of brightness value and a window width value for contrast. In an exemplary embodiment, the data provision unit 128 may be configured to determine a first value for a center of brightness and/or a second value for a window width for contrast prior to processing the retrieved requested image. These values may be determined from the request received from the client device 102. Additionally or alternatively, the data provision unit 128 may be configured to determine a value for a center of brightness and/or a value for a window width for contrast from information associated with the image, such as, for example may be found in a DICOM header. The data provision unit 128 may then be configured to process the request image to generate the image having reduced bit-depth based at least in part upon the determined value for a center of brightness and/or the determined value for a window width for contrast.

The data provision unit 128 may then provide the reduced-bit image to the client device 102 so that a user may view and manipulate the reduced-bit image on a general purpose viewing agent 118 embodied on the client device 102. The data provision unit may further be configured to receive a request for another image from the client device 102. The request for the additional image may comprise a request for another reduced bit-depth snapshot of the original requested image. In this regard, a user of the client device 102 may desire to manipulate the previously sent image beyond the limits of the image. Accordingly, the data provision unit 128 may be configured to process the original source image to generate another reduced-bit image (e.g., a third image) based upon a different value for a center of brightness and/or a different value for a window width for contrast than was used to generate the first reduced-bit image. The data provision unit 128 may be configured to determine the new value(s) for a center of brightness and/or a window width for contrast from the request or may automatically determine a new value(s) based upon a predefined offset from the originally used value(s). The data provision unit 128 may then be configured to provide the third image to the client device 102 such that the previously provided second image may be replaced with the third image to facilitate viewing and manipulation of the third image by a user using a general purpose viewing agent 118 embodied on the client device 102.

In one embodiment, the data provision unit 128 may further be configured to store each generated reduced-bit image in a memory, such as memory 122. The data provision unit 128 may be configured to determine in such an embodiment whether an appropriate previously generated reduced-bit image is stored in memory each time a request for an image is received. In this regard, each stored reduced-bit image may be stored, such as in a database, in association with the source image from which it was generated as well as an indication of a center of brightness value and/or a window width for contrast value associated with the stored reduced-bit image. Accordingly, if the data provision unit 128 receives a request for an image having a center of brightness value and/or a window width for contrast value determined by the data provision unit 128, the data provision unit 128 may be configured to search memory for a stored reduced-bit image matching the request parameters. In this regard, if the data provision unit 128 finds a stored reduced-bit image having the determined center of brightness value and/or window width for contrast value, the data provision unit 128 may provide the stored reduced-bit image to the client device 102 rather than processing the original image to generate another reduced-bit image.

In an exemplary embodiment, the data provision unit 128 may be configured to provide a DICOM-HTTP interface. In this regard, firewalls may pose difficulties in interfacing across institutions, such as between a data server 104 and client device 102, one or more of which may reside on a private network not including the other device. For example, although not illustrated in FIG. 1, one or more firewalls may be embodied on the network 106 between the data server 104 and client device 102. IT departments may be reluctant to open up ports on firewalls for security purposes. However, most firewalls have at least one web port open so as to facilitate HTTP traffic. The data provision unit 128 may be configured to receive a DICOM file from a DICOM source (e.g., memory 122 and/or another device or memory accessible by the data server 104) and then forward the DICOM files to an external computing device or server (e.g., a client device 102) outside the firewall via HTTP or HTTPS post over a standard web or secure sockets layer (SSL) port. Additionally or alternatively, the data provision unit 128 may be configured to forward the DICOM files via DICOM communications standards over a standard web or SSL port. In this regard, the data provision unit 128 may provide DICOM files directly to a client device 102 in instances where the client device comprises hardware or a software application configured to view and manipulate DICOM files. Also, the data provision unit 128 may serve as a relay, such as may be found on a network entity to interface between a data server and a client device 102 for purposes of formatting data traffic such that it may be sent to a computing device external to a firewall without altering security settings. In this regard, the data provision unit 128 or at least the operating logic and/or hardware necessary to implement the DICOM-HTTP interface may be embodied on a computing device other than data server 104.

The data provision unit 128 may further be configured to anonymize each file, such as, for example, a DICOM file so as to remove sensitive data, such a patient data that may be associated with the file. This anonymization may be based upon a configuration setting. Additionally or alternatively, the data provision unit 128 may be configured to determine an appropriate level of anonymization based at least in part upon an identity of a requesting client device 102, a user thereof, and/or a level of security associated with a network over which the file will be transmitted. The data provision unit 128 may be configured to post files one at a time or package multiple files up in a container and post the multiple files in bulk. The data provision unit 128 may further be configured to compress files for quicker transmission.

In an exemplary embodiment, the data provision unit 128 may further be send data, such as requested images, as a data stream (e.g., an HTTP data stream) containing a series of delimited messages. These delimited messages may be generated by the data provision unit 128 and may be defined by a character sequence. Accordingly, a client device 102 receiving the series of delimited messages may not need to wait for the requested data to be received and parsed in its entirety before taking action on the individual delimited messages. Additionally, the use of a series of delimited messages may be beneficial in that it may avoid a need to use a secondary data port to transmit streaming data that may be blocked by firewalls and instead allows for the data stream to be sent over an HTTP or HTTPS port.

FIG. 3 is a flowchart of a system, method, and computer program product according to an exemplary embodiment of the invention. It will be understood that each block or step of the flowchart, and combinations of blocks in the flowchart, may be implemented by various means, such as hardware, firmware, and/or software including one or more computer program instructions. For example, one or more of the procedures described above may be embodied by computer program instructions. In this regard, the computer program instructions which embody the procedures described above may be stored by a memory device of a mobile terminal, server, or other computing device and executed by a processor in the computing device. In some embodiments, the computer program instructions which embody the procedures described above may be stored by memory devices of a plurality of computing devices. As will be appreciated, any such computer program instructions may be loaded onto a computer or other programmable apparatus to produce a machine, such that the instructions which execute on the computer or other programmable apparatus create means for implementing the functions specified in the flowchart block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions, combinations of steps for performing the specified functions and program instruction means for performing the specified functions. It will also be understood that one or more blocks or steps of the flowcharts, and combinations of blocks or steps in the flowchart, may be implemented by special purpose hardware-based computer systems which perform the specified functions or steps, or combinations of special purpose hardware and computer instructions.

Figure 4:
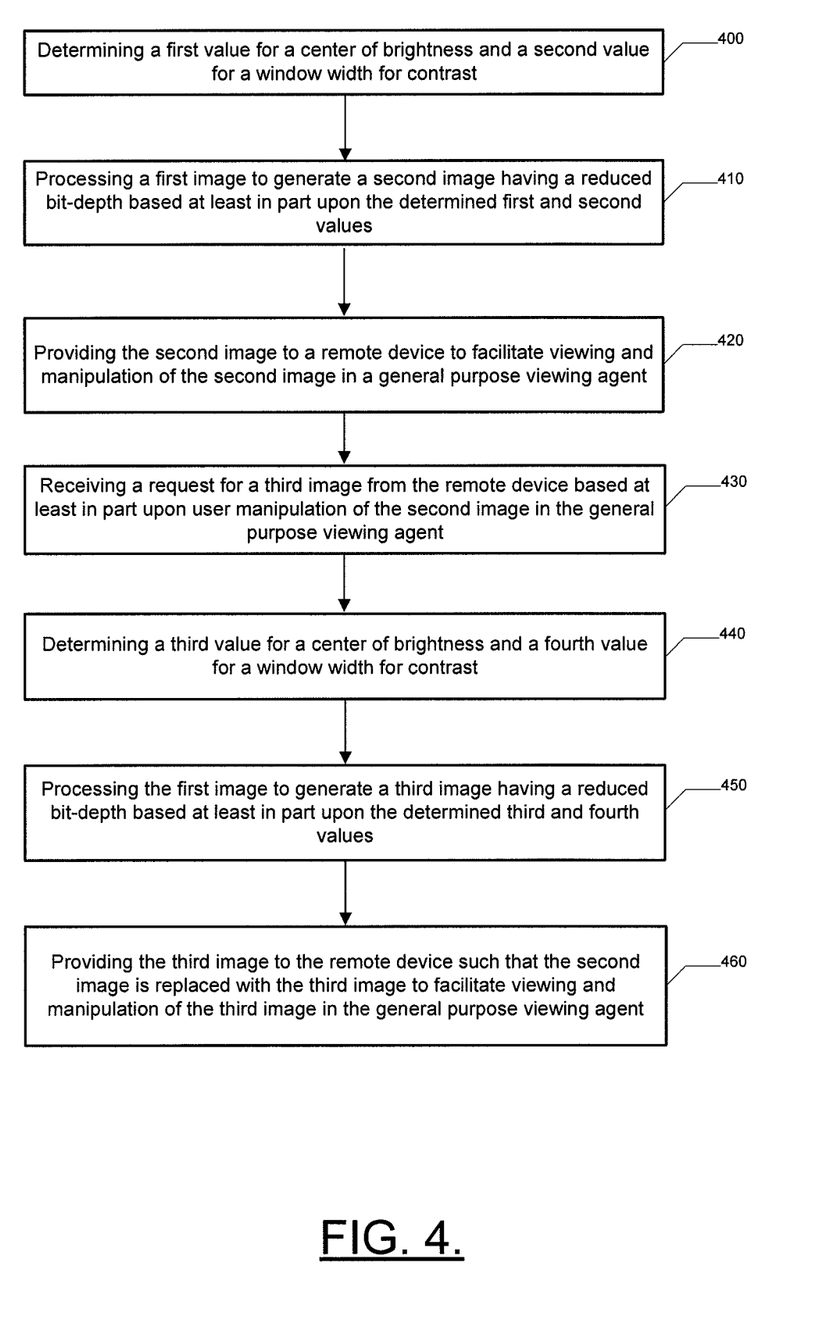
FIG. 4 is a flowchart according to an exemplary method for transmitting, viewing, and manipulating images in a general purpose viewing agent according to an exemplary embodiment of the present invention.

In this regard, one exemplary method for transmitting, viewing, and manipulating images in a general purpose viewing agent according to an exemplary embodiment of the present invention is illustrated in FIG. 4. The method may include the data provision unit 128 determining a first value for a center of brightness and a second value for a window width for contrast at operation 400. Operation 410 may comprise the data provision unit 128 processing a first image to generate a second image having a reduced bit-depth based at least in part upon the determined first and second values. The data provision unit 128 may provide the second image to a remote device to facilitate viewing and manipulation of the second image in a general purpose viewing agent at operation 420. Operation 430 may comprise the data provision unit 128 receiving a request for a third image from the remote device based at least in part upon user manipulation of the second image in the general purpose viewing agent. Operation 440 may comprise the data provision unit 128 determining a third value for a center of brightness and a fourth value for a window width for contrast. The data provision unit 128 may then process the first image to generate a third image having a reduced bit-depth based at least in part upon the determined third and fourth values at operation 450. Operation 460 may comprise the data provision unit 128 providing the third image to the remote device such that the second image is replaced with the third image to facilitate viewing and manipulation of the third image in the general purpose viewing agent.

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, some embodiments of the invention may provide several advantages to a user of a computing device seeking to view and manipulate data, such as medical images in a general purpose viewing agent. Embodiments of the invention may provide a rich user interface without requiring software to be downloaded and installed on a general purpose viewing agent, such as a web browser, beyond what is already present on a large majority of browsers. Accordingly, embodiments of the present invention may work instantly with any browser on any platform, without requiring installation of additional specialized software components. In this regard, embodiments of the present invention may provide a general solution that leverages general purpose viewing agents along with general graphics/animation services, such as Flash®, that are either natively available or which are widely installed in general purpose viewing agents. Thus, embodiments of the invention may offer Picture Archiving and Communication System (PACS)-like functionality in a true thin client, without requiring the installation and execution of special purpose software on a client device that would otherwise be necessary for viewing and manipulating higher resolution, specially formatted data and images that may be archived on data servers, such as PACS servers.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   determining a first value for a center of brightness and a second value for a window width for contrast;
   processing, by a processor of a first device, a first image to generate a second image having a reduced bit-depth based at least in part upon the determined first and second values;
   providing the second image from the first device to a remote client device over a network to facilitate viewing and manipulation of the second image in a web browser on the client device;
   receiving an indication that the second image has been manipulated so that at least one of a brightness value or a contrast value associated with the second image is adjusted beyond a threshold value;
   in response to receiving the indication that the brightness value or contrast value associated with the second image is adjusted beyond the threshold value, determining a third value for a center of brightness and a fourth value for a window width for contrast, and processing the first image to generate a third image having a reduced bit-depth based at least in part upon the determined third and fourth values; and
   providing the third image to the client device such that the second image is replaced with the third image to facilitate viewing and manipulation of the third image in the web browser.

2. A method according to claim 1, further comprising receiving a request for the third image from the client device based at least in part upon user manipulation of the second image in the web browser.

3. A method according to claim 1, wherein determining the first and second values comprises determining the first and second values based at least in part upon an indication received from a user of the client device.

4. A method according to claim 1, wherein determining the first and second values comprises determining the first and second values based at least in part upon information associated with the first image.

5. A method according to claim 1, wherein the first image is a medical image formatted in accordance with the Digital Imaging and Communications in Medicine standard data format.

6. A method according to claim 1, wherein manipulation of the second image comprises adjusting one or more of a brightness level or a contrast level associated with the second image.

7. A method according to claim 1, wherein providing the second image to the client device comprises sending the second image as a series of delimited messages that can be handled independently, so that the client device does not have to wait for the entire second image to be received and parsed prior to beginning to render the second image.

8. A computer program product comprising at least one non-transitory computer-readable storage medium having computer-readable program instructions stored therein, the computer-readable program instructions comprising:

a first program instruction for determining a first value for a center for brightness and a second value for a window width for contrast;

a second program instruction for processing, at a first device, a first image to generate a second image having a reduced bit-depth based at least in part upon the determined first and second values;

a third program instruction for providing the second image from the first device to a remote client device over a network to facilitate viewing and manipulation of the second image in a web browser on the client device;

a fourth program instruction for receiving an indication that the second image has been manipulated so that a brightness value or a contrast value associated with the second image is adjusted beyond a threshold value;

a fifth program instruction for, in response to receiving the indication that the brightness value or contrast value associated with the second image is adjusted beyond the threshold value, determining a third value for a center of brightness and a fourth value for a window width for contrast, and processing the first image to generate a third image having a reduced bit-depth based at least in part upon the determined third and fourth values; and a sixth program instruction for providing the third image to the client device such that the second image is replaced with the third image to facilitate viewing and manipulation of the third image in the web browser.

9. A computer program product according to claim 8, further comprising a seventh program instruction for receiving a request for the third image from the client device based at least in part upon user manipulation of the second image in the web browser.

10. An apparatus comprising a processor configured to:

determine a first value for a center of brightness and a second value for a window width for contrast;

process a first image to generate a second image having a reduced bit-depth based at least in part upon the determined first and second values;

provide the second image to a remote client device over a network to facilitate viewing and manipulation of the second image in a web browser on the client device;

receive an indication that the second image has been manipulated so that a brightness value or a contrast value associated with the second image is adjusted beyond a threshold value;

in response to receiving the indication that the brightness value or contrast value associated with the second image is adjusted beyond the threshold value, determine a third value for a center of brightness and a fourth value for a window width for contrast, and process the first image to generate a third image having a reduced bit-depth based at least in part upon the determined third and fourth values; and provide the third image to the client device such that the second image is replaced with the third image to facilitate viewing and manipulation of the third image in the web browser.

11. An apparatus according to claim 10, wherein the processor is further configured to receive a request for the third image from the client device based at least in part upon user manipulation of the second image in the web browser.

12. An apparatus according to claim 10, wherein the processor is configured to determine the first and second values based at least in part upon an indication received from a user of the client device.

13. An apparatus according to claim 10 wherein the processor is configured to determine the first and second values based at least in part upon information associated with the first image.

14. An apparatus according to claim 10 wherein the first image is a medical image formatted in accordance with the Digital Image and Communications in Medicine standard data format.

15. An apparatus according to claim 10 wherein manipulation of the second image comprises adjusting one or more of a brightness level or a contrast level associated with the second image.

16. An apparatus according to claim 10, wherein the processor is configured to provide the second image to the client device by sending the second image as a series of delimited messages that can be handled independently, so that the client device does not have to wait for the entire second image to be received and parsed prior to beginning to render the second image.

17. A system comprising:

a host device configured to (i) receive, via a network, a request for a medical image from a client device, (ii) determine a first value for a center of brightness and a second value for a window width for contrast, (iii) process the requested medical image to generate a second image having a reduced bit-depth based at least in part upon the determined first and second values, (iv) provide the second image to the client device over the network, (v) receive an indication that the second image has been manipulated so that a brightness value or a contrast value associated with the second image is adjusted beyond a threshold value, (vi) in response to receiving the indication that the brightness value or contrast value associated with the second image is adjusted beyond the threshold value, determine a third value for a center of brightness and a fourth value for a window width for contrast, and process the first image to generate a third image having a reduced bit-depth based at least in part upon the determined third and fourth values, and (vii) provide the third image to the client device such that the second image is replaced with the third image to facilitate viewing and manipulation of the third image in the web browser; and the client device is further configured to request a third image from the host device; and a client device configured to request a medical image from the host device and to receive the second image, wherein the client device comprises a web browser for facilitating viewing and manipulation of the second image by a user of the client device.

18. The system of claim 17, wherein:

the host device is further configured to receive a request for the third image from the client device based at least in part upon manipulation of the second image in the web browser.

* * * * *